United States Patent
Yam et al.

(10) Patent No.: US 8,987,450 B2
(45) Date of Patent: Mar. 24, 2015

(54) LUMINESCENT GOLD(III) COMPOUNDS FOR ORGANIC LIGHT-EMITTING DEVICES AND THEIR PREPARATION

(71) Applicant: The University of Hong Kong, Hong Kong (CN)

(72) Inventors: Vivian Wing-Wah Yam, Hong Kong (CN); Vonika Ka-Man Au, Hong Kong (CN); Mei-Yee Chan, Hong Kong (CN); Keith Man-Chung Wong, Hong Kong (CN); King Chin Yim, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 13/838,185

(22) Filed: Mar. 15, 2013

(65) Prior Publication Data

US 2013/0193428 A1 Aug. 1, 2013

Related U.S. Application Data

(63) Continuation-in-part of application No. 12/494,765, filed on Jun. 30, 2009, now Pat. No. 8,415,473, which is a continuation-in-part of application No. 10/977,200, filed on Oct. 29, 2004, now Pat. No. 7,572,912.

(51) Int. Cl.
*C07F 1/12* (2006.01)
*H01L 51/50* (2006.01)
*H01L 51/00* (2006.01)
*C09K 11/06* (2006.01)
*H05B 33/14* (2006.01)
*C07F 1/00* (2006.01)

(52) U.S. Cl.
CPC ............ *H01L 51/0084* (2013.01); *C09K 11/06* (2013.01); *H01L 51/0091* (2013.01); *H05B 33/14* (2013.01); *C07F 1/005* (2013.01); *C07F 1/12* (2013.01); *H01L 51/0081* (2013.01); *H01L 51/5016* (2013.01); *C09K 2211/1007* (2013.01); *C09K 2211/1029* (2013.01); *C09K 2211/188* (2013.01)
USPC ................................ 546/2; 313/504; 548/108

(58) Field of Classification Search
USPC ................................ 546/2; 548/108; 313/504
See application file for complete search history.

(56) References Cited

PUBLICATIONS

Serratrice, M. et al.: Cytotoxic gold compounds: synthesis, biological characterization and investigation of their inhibition properties of the zinc finger protein PARP-1. Dalton Transactions, vol. 41, pp. 3287-3293, 2012.*

* cited by examiner

*Primary Examiner* — Charanjit Aulakh
(74) *Attorney, Agent, or Firm* — Saliwanchik, Lloyd & Eisenschenk (57) ABSTRACT

In one embodiment, the present invention provides a class of luminescent gold(III) compounds containing a tridentate ligand with one strong σ-donating group. The present invention also provides methods for synthesizing these compounds, as well as uses of these compounds as electrophosphorescent materials in phosphorescent organic light-emitting devices (OLEDs) to provide electroluminescence (EL).

12 Claims, 1 Drawing Sheet

FIG. 1 Electronic absorption spectra of 4, 6 and 7 in dichloromethane at 298 K.

FIG. 2 EL intensity of devices with 2 doped in MCP as light-emitting layer.

LUMINESCENT GOLD(III) COMPOUNDS FOR ORGANIC LIGHT-EMITTING DEVICES AND THEIR PREPARATION

CROSS-REFERENCE TO RELATED APPLICATIONS

This application is a continuation-in-part of U.S. application Ser. No. 12/494,765, filed Jun. 30, 2009, which is a continuation-in-part of U.S. Pat. No. 7,572,912, issued Aug. 11, 2009, which are hereby incorporated by reference in their entirety to the extent that they are not inconsistent with explicit teachings herein.

FIELD OF THE INVENTION

The present invention relates to the design and synthesis of novel classes of gold(III) compounds containing a tridentate ligand with one strong σ-donating group. Such compounds can be used as light-emitting material in phosphorescent organic light-emitting devices.

BACKGROUND

There has been an enormous increase in research interest towards the development of organic light-emitting devices (OLEDs) after the first report of double-layer structured OLED devices by Tang and vanSlyke [Tang, C. W.; vanSlyke, S. A. Appl. Phys. Lett. 51, 913 (1987)]. OLEDs have been demonstrated to be attractive candidates for flat panel displays owing to their distinct advantages including low operating voltage, low energy consumption, high brightness, high robustness, color tunability, wide viewing angle, relatively low cost, as well as ease of fabrication onto a variety of substrates.

A typical OLED contains several layers of semiconductor sandwiched between two electrodes. The cathode is composed of a low work function metal alloy deposited by vacuum evaporation, whereas the anode is a transparent conductor such as indium tin oxide (ITO). Upon the application of a DC voltage, holes injected by the ITO electrode and electrons injected by the metal electrode will recombine within the semiconductor to form excitons. Subsequent relaxation of excitons will then result in the generation of electroluminescence (EL).

Over the last two decades, an increasing attention has been drawn towards the use of phosphorescent materials, especially transition metal compounds, for the fabrication of OLEDs. In the presence of a heavy metal center, the chance of spin-orbit coupling can be greatly enhanced to facilitate the mixing of singlet and triplet excited states. This yields to a four-fold increase on the internal quantum efficiency of up to 100%. In order to obtain higher EL efficiencies, the use of heavy metal compounds in OLEDs is preferred over purely organic materials, in which the lowest energy excited state of an organometallic compound is commonly a metal-to-ligand charge transfer (MLCT) triplet state, mixed with the excited singlet state through L-S coupling [Baldo, M. A.; Thompson, M. E.; Forrest, S. R. Pure Appl. Chem. 71, 2095 (1999)]. In 1998, Baldo et al. demonstrated a phosphorescent EL device with high quantum efficiency by using platinum(II) 2,3,7,8,12,13,17,18-octaethyl-21H,23H-porphine (PtOEP) as the dopant. In a multilayer device using tris(8-hydroxyquinoline) aluminium (Alq₃) doped with varying concentrations of PtOEP in the light-emitting layer, a strong emission at 650 nm attributed to the triplet excitons of PtOEP was observed [Baldo, M. A.; O'Brien, D. F.; You, Y.; Shoustikow, A.; Sibley, S.; Thompson, M. E.; Forrest, S. R. Nature 395, 151 (1998)].

Later, Baldo et al. also reported the use of fac-tri(2-phenylpyridine)iridium(III) [Ir(ppy)₃] as phosphorescent emitting material which was doped in 4,4'-N,N'-diarbazole-biphenyl (CBP) as a host in an OLED to give high quantum efficiency [Baldo, M. A.; Lamansky, S.; Burrows, P. E.; Thompson, M. E.; Forrest, S. R. Appl. Phys. Lett. 75, 4 (1999)].

To date, although much work has been reported on electrophosphorescent materials based on transition metal compounds, most of them have been focused on the use of heavy metal centers such as iridium(III), platinum(II) and ruthenium(II), whereas the use of other metal centers have been much less explored. In particular, in contrast to the isoelectronic platinum(II) compounds which are known to show rich luminescence properties, very few examples of luminescent gold(III) compounds have been reported, probably due to the presence of low-energy d-d ligand field (LF) states and the electrophilicity of the gold(III) metal center. One way to enhance luminescence of gold(III) compounds is through the introduction of strong σ-donating ligands, which was first demonstrated by Yam et al. in which stable gold(III) aryl compounds were synthesized and found to display interesting photoluminescence properties even at room temperature [Yam, V. W. W.; Choi, S. W. K.; Lai, T. F.; Lee, W. K. J. Chem. Soc., Dalton Trans. 1001 (1993)]. Yam et al. later synthesized a series of bis-cyclometalated alkynylgold(III) compounds using various strong σ-donating alkynyl ligands to yield compounds with rich luminescence at both room and low temperatures in various media [Yam, V. W.-W.; Wong, K. M.-C.; Hung, L.-L.; Zhu, N. Angew. Chem. Int. Ed. 44, 3107 (2005); Wong, K. M.-C.; Hung, L.-L.; Lam, W. H.; Zhu, N.; Yam, V. W.-W. J. Am. Chem. Soc. 129, 4350 (2007); Wong, K. M.-C.; Zhu, X.; Hung, L.-L.; Zhu, N.; Yam, V. W.-W.; Kwok, H. S. Chem. Commun. 2906 (2005)].

BRIEF SUMMARY OF THE INVENTION

The present invention is directed to novel luminescent cyclometalated gold(III) compounds, their preparations, and OLEDs containing them. Described below are the design and synthesis of various novel gold(III) compounds.

The objective of the present invention is to provide a novel class of cyclometalated gold(III) compounds for applications in OLEDs. The invented gold(III) compound is a coordination compound that contains a tridentate cyclometalated ligand and at least one strong σ-donating group, both coordinated to a gold(III) metal center. There is no restriction on the nature of the aryl groups in the cyclometalated ligands and they can be heteroaryl groups such as, for instance, thienyl groups. Likewise, any σ-donating group can be employed as the ancillary ligand, for instance, alkynyl groups, aryl groups, heteroaryl groups, N-heterocyclic carbenes.

In one embodiment, the present invention provides compounds having the chemical structure represented by the following general formula (I), wherein:
(a) X, Y and Z are independently carbon or nitrogen;
(b) A, B and C are cyclic structures;
(c) any combinations of the rings A, B and C can be fused together with each other or the rings A, B and C can be non-fused with each other;
(d) A is selected from unsubstituted or substituted pyridine, benzene, naphthalene, imidazole, benzimidazole, pyrrole, isoquinoline, pyrimidine, pyrazine, pyrazole, triazole, tetrazole, pyridazine, triazine, tetrazine, and N-heterocyclic carbene;
(e) B and C are independently selected from unsubstituted or substituted pyridine, benzene, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene;
(f) $R_1$ is an optionally substituted σ-donor ligand attached to the gold atom;
(g) n is zero, a positive integer or a negative integer;
with proviso that when A is unsubstituted or substituted pyridine,
1) at least one of Y or Z is not carbon, or
2) at least one of B or C is selected from unsubstituted or substituted pyridine, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene.

In one embodiment of the compounds of formula (I), when X is carbon, at least one of B and C is not substituted or unsubstituted benzimidazole. In another embodiment of the compounds of formula (I), when X is carbon, both B and C are not substituted or unsubstituted benzimidazole.

In one embodiment of the compounds of formula (I), when X is nitrogen, at least one of B and C is not substituted or unsubstituted imidazole. In another embodiment of the compounds of formula (I), when X is nitrogen, both B and C are not substituted or unsubstituted imidazole.

The luminescent gold(III) compounds of the present invention can exhibit photoluminescence via triplet excited state upon photo-excitation, or generate EL via triplet exciton upon applying a DC voltage. Exemplified compounds of the present invention, having luminescence properties, include Compounds 1-13. Preferred compounds of the invention are thermally stable and volatile enough to be able to form a thin layer by sublimation or vacuum deposition. Alternatively, the compounds can be doped into a host matrix for thin film deposition by spin-coating or inkjet printing or other known fabrication methods.

In one embodiment, the present invention is also directed to the use of luminescent compounds of general formula (I) as phosphorescent emitters or dopants for the fabrication of OLEDs to generate EL.

In an embodiment of the OLED according to the present invention, the luminescent gold(III) compound is included in a light-emitting layer. In one embodiment, a typical structure of an OLED, comprising luminescent compounds of the present invention as a light-emitting layer, is in the following order: cathode/electron transporting layer/luminescent gold (III) compound as a light-emitting layer/hole transporting layer/anode.

DETAILED DESCRIPTION OF THE INVENTION

The present invention provides a class of luminescent gold (III) compounds with one tridentate ligand and one strong σ-donating group, the synthesis and luminescence studies of such compounds, and the use of such compounds as light-emitting material in OLEDs to provide EL with high efficiency and brightness.

In one embodiment, the present invention provides compounds having the following structural characteristics:
(1) at least one gold metal center at an oxidation state of +3;
(2) the said gold metal center having four coordination sites;
(3) one tridentate ligand with one to three aromatic or heterocyclic ring(s) coordinating to the gold metal center;
(4) one monodentate ligand coordinating to the gold metal center;
(5) at least one strong σ-donating ligand coordinating to the gold metal center; and
(6) the compounds being charged or neutral.

In one embodiments, the present invention provides compounds having the chemical structure represented by the following general formula (I), wherein:
(a) X, Y and Z are independently carbon or nitrogen;
(b) A, B and C are cyclic structures;
(c) any combinations of the rings A, B and C can be fused together with each other or the rings A, B and C can be non-fused with each other;
(d) A is selected from unsubstituted or substituted pyridine, benzene, naphthalene, imidazole, benzimidazole, pyrrole, isoquinoline, pyrimidine, pyrazine, pyrazole, triazole, tetrazole, pyridazine, triazine, tetrazine, and N-heterocyclic carbene;
(e) B and C are independently selected from unsubstituted or substituted pyridine, benzene, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene;

(f) R₁ is an optionally substituted σ-donor ligand attached to the gold atom;

(g) n is zero, a positive integer or a negative integer;

with proviso that when A is unsubstituted or substituted pyridine, 1) at least one of Y or Z is not carbon, or 2) at least one of B or C is selected from unsubstituted or substituted pyridine, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene.

In one embodiment of the compounds of formula (I), when X is carbon, at least one of B and C is not substituted or unsubstituted benzimidazole. In another embodiment of the compounds of formula (I), when X is carbon, both B and C are not substituted or unsubstituted benzimidazole.

In one embodiment of the compounds of formula (I), when X is nitrogen, at least one of B and C is not substituted or unsubstituted imidazole. In another embodiment of the compounds of formula (I), when X is nitrogen, both B and C are not substituted or unsubstituted imidazole.

In certain embodiments of the compounds of formula (I), when X is nitrogen, 1) at least one of Y or Z is not carbon, or 2) at least one of B or C is selected from unsubstituted or substituted pyridine, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene.

In one embodiment, n is the charge on the compound of formula (I). In certain embodiments, n is zero for a neutral compound, or is a positive integer or a negative integer where the compound is the cation or anion, respectively, of a salt. In certain embodiments, n is selected from −3, −2, −1, 0, 1, 2, and 3.

In certain embodiments of the compounds of formula (I), when X is nitrogen, B and C are independently selected from unsubstituted or substituted pyridine, benzene, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene.

In certain embodiments of the compounds of formula (I), when X is carbon, B and C are independently selected from unsubstituted or substituted pyridine, benzene, naphthalene, anthracene, pyrene, imidazole, benzimidazole, thiazole, oxazole, benzothiazole, benzoxazole, pyrrole, isoquinoline, quinoline, carbazole, fluorene, pyrimidine, pyrazine, pyrazole, triazole, tetrazole, isoxazole, isothiazole, pyridazine, indole, pyran, thiapyran, oxadiazole, triazine, tetrazine, dibenzothiophene, dibenzofuran, and N-heterocyclic carbene.

In certain embodiments, R₁ is selected from, but is not limited to, alkylalkynyl, substituted alkylalkynyl, arylalkynyl, substituted arylalkynyl, heteroarylalkynyl, substituted heteroarylalkynyl, polyalkynyl, substituted polyalkynyl, aryl, substituted aryl, substituted heteroaryl, heteroaryl, hydroxyl, alkoxyl, substituted alkoxyl, aryloxyl, substituted aryloxyl, cycloalkoxyl, substituted cycloalkoxyl, $NH_2$, unsubstituted and substituted primary amine, unsubstituted and substituted secondary amine, unsubstituted and substituted tertiary amine, carboxamide, substituted carboxamide, amide, substituted amide, imide, substituted imide, nitrile, substituted nitrile, isonitrile, substituted isonitrile, sulfanyl, sulfinyl, substituted sulfinyl, sulfonyl, and substituted sulfonyl.

In certain embodiments, rings A, B and C are independently selected from a 5- or 6-membered arene, heteroarene or heterocycle known in the art. Preferred arenes or heteroarenes are substituted and unsubstituted benzene, pyridine, imidazole, benzimidazole, oxazole, benzoxazole, thiazole, benzothiazole, thiophene, benzothiophene, furan, benzofuran, pyrazole, isoxazole, isothiazole, isoquinoline, quinoline, pyrrole, pyrazine, pyridazine, pyrimidine, indole, naphthalene, anthracene, pyrene, triazole, tetrazole, pyran, thiapyran, oxadiazole, triazine, tetrazine, carbazole, dibenzothiophene, dibenzofuran, and fluorene.

In certain embodiments, rings A, B and C are optionally substituted with one or more substituents selected from hydrogen, deuterium, alkyl, heteroalkyl, alkenyl, cycloalkenyl, heteroalkenyl, alkynyl, alkylaryl, aryl, cycloalkyl, CN, $CF_3$, $NO_2$, $SO_2$, halo, hydroxyl, alkoxyl, aryloxyl, cycloalkoxyl, ester, ether, amide, imide, $NH_2$, primary amine, secondary amine, tertiary amine, sulfanyl, sulfinyl, sulfonyl, heteroaryl, silyl, acyl, carbonyl, carboxylic acid, nitrile, isonitrile, phosphine and combinations thereof. The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below.

The term "halo" or "halogen" as used herein includes fluorine, chlorine, bromine and iodine.

The term "alkyl" as used herein includes both straight and branched chain alkyl groups. Preferred alkyl groups are those containing from one to eighteen carbon atoms and include methyl, ethyl, propyl, isopropyl, butyl, isobutyl, tert-butyl, and the like. In addition, the alkyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "alkenyl" as used herein includes both straight and branched chain alkene radicals. Preferred alkenyl groups are those containing two to eighteen carbon atoms. In addition, the alkenyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "alkynyl" as used herein includes both straight and branched chain alkyne radicals. Preferred alkynyl groups are those containing two to eighteen carbon atoms. In addition, the alkynyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "arylalkynyl" as used herein includes an alkynyl group which has an aromatic group as a substituent. In addition, the arylalkynyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "alkylaryl" as used herein includes an alkyl group which has an aromatic group as a substituent. In addition, the alkylaryl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "cycloalkyl" as used herein includes cyclic alkyl groups. Preferred cycloalkyl groups are those containing 3 to 7 carbon atoms and include cyclopropyl, cyclopentyl, cyclohexyl, and the like. In addition, the cycloalkyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "alkoxyl" as used herein includes both straight and branched chain alkyl groups attached to the parent structure through an oxygen atom. Preferred alkoxyl groups are those containing from one to eighteen carbon atoms and include methoxy, ethoxy, propoxy, isopropoxy, and the like. In addition, the alkoxyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "cycloalkoxyl" as used herein includes cyclic alkoxyl groups. Preferred cycloalkyl groups are those containing 3 to 7 carbon atoms and include cyclopropyloxyl, cyclohexyloxyl, and the like. In addition, the cycloalkoxyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

The term "arylalkoxyl" as used herein includes an aromatic group attached to the parent structure through an oxygen atom. Preferred arylalkoxyl groups are those containing 3 to 7 carbon atoms and include phenoxyl, and the like. In addition, the aryloxyl group may be optionally substituted with one or more substituents selected from alkoxyl, amino, thiol, alkylcarbonyl, alkoxycarbonyl, alkylaminocarbonyl, CN, $CF_3$, $NO_2$, $SO_2$, alkylsulfonyl, alkylsulfinyl, alkylsulfuryl, halo and cyclic-amino.

Preferred alkyl groups are $C_1$ through $C_{18}$ alkyls. Similarly $C_1$ through $C_{18}$ alkoxy and aryl groups are preferred. $C_1$ through $C_{18}$ heteroaryl, alkylamino, arylamino, alkylsulfido, arylsulfido, alkylphosphino or arylphosphino groups are preferred.

Aryl alone or in combination includes carbocyclic aromatic systems. The systems may contain one, two or three rings wherein each ring may be attached together in a pendent manner or may be fused. Preferably the rings are 5- or 6-membered rings.

Heteroaryl alone or in combination includes heterocyclic aromatic systems. The systems may contain one, two or three rings wherein each ring may be attached together in a pendent manner or may be fused. Preferably the rings are 5- or 6-membered rings.

Heterocyclic and heterocycle refer to a 3- to 7-membered ring containing at least one heteroatom. This includes aromatic rings including, but not limited to, pyridine, thiophene, benzothiophene, furan, pyrazole, imidazole, oxazole, benzoxazole, isoxazole, thiazole, isothiazole, isoquinoline, quinoline, pyrrole, pyrazine, pyridazine, pyrimidine, benzimidazole, benzofuran, thiazole, benzothiazole, indole, naphthalene, triazole, tetrazole, pyran, thiapyran, oxadiazole, triazine, tetrazine, carbazole, dibenzothiophene, dibenzofuran, indole, fluorene; and non-aromatic rings including, but not limited to, piperazine, piperidine, and pyrrolidine. The groups of the present invention can be substituted or unsubstituted. Preferred substituents include, but are not limited to, alkyl, alkoxy, and aryl.

Heteroatom refers to an atom of any element other than carbon or hydrogen. Preferred heteroatoms include, but are not limited to, oxygen, nitrogen, phosphorus and sulfur.

Substituted refers to any level of substitution although mono-, di- and tri-substitutions are preferred. Preferred substituents include, but are not limited to, halogen, aryl, alkyl and heteroaryl.

Unsubstituted refers to any open valence of an atom being occupied by hydrogen. If an occupant of an open valence position on an atom is not specified then it is hydrogen.

N-Heterocyclic carbene (NHC), a term well known in the art, refers to a type of diaminocarbene in which the carbenic carbon is part of a nitrogen-containing heterocycle, such as imidazole or benzimidazole. NHC includes but is not limited to 1,3-dimethylimidazol-2-ylidene (IMe), 1,3-dimethylbenzimidazol-2-ylidene (BIMe), 1,3-dimesitylimidazol-2-ylidene (IMes), 1,3-dimesityl-4,5-dihydroimidazol-2-ylidene (SIMes), 1,2-bis(3-methylimidazolium-1-yl)ethane ($MeIC_2IMe$), 1,4-bis(3-methylimidazolium-1-yl)butane ($MeIC_4IMe$), 1,6-bis(3-methylimidazolium-1-yl)hexane ($MeIC_6IMe$) and 2,6-bis(1-methylimidazolium-3-yl)pyridine (MeICBCIMe).

As used herein, the term "carbene" is a molecule comprising a neutral carbon atom with a valence of two, and two valence electrons available for formation of a dative bond.

Emission of gold(III) compounds is rarely observed in contrast to the isoelectronic platinum(II) systems which are known to possess rich luminescence properties. The lack of luminescence in gold(III) compounds is probably due to the presence of low-lying d-d ligand field (LF) states as well as the electrophilicity of the gold(III) metal center. In order to enhance the luminescence of gold(III) compounds, it is believed that one could incorporate strong σ-donating ligands to the gold(III) metal center to make it more electron-rich, thereby raising the energy of the d-d LF states and thus increasing the chances for population of the emissive state. Gold(III) compounds with exceptionally interesting luminescence properties have been reported in the literature. For instance, a series of gold(III) aryl compound was found to show interesting luminescence properties even at room temperature and were stable upon light irradiation [Yam et al. *J. Chem. Soc., Dalton Trans.* 1001 (1993)]. Later on, a class of luminescence biscyclometalated alkynylgold(III) compound has been reported, in which strong σ-donating alkynyl groups have been incorporated into the gold(III) metal center to improve the emission properties. These compounds were found to be emissive at both room and low temperatures in various media [Yam et al. *Angew. Chem. Int. Ed.* 44, 3107 (2005); Wong et al. *J. Am. Chem. Soc.* 129, 4350 (2007)].

Related biscylometalated gold(III) N-heterocyclic carbene compounds with rich luminescence properties have also been reported [Au et al. *J. Am. Chem. Soc.* 131, 9076 (2009)], in which the N-heterocyclic carbene moiety functions as a strong σ-donor to enhance the emission properties. The use of such alkynylgold(III) compounds as electrophosphorescent emitters or dopants of OLEDs has been communicated in the literature [Wong et al. *Chem. Commun.* 2906 (2005); Au et al. *J. Am. Chem. Soc.* 132, 14273 (2010)].

In addition to those gold(III) compounds with tridentate cyclometalated ligands reported in U.S. Pat. No. 7,572,912 B2, issued Aug. 11, 2009, and U.S. application Ser. No. 12/494,765, filed Jun. 30, 2009, the present invention will employ various new tridentate ligands as well as a variety of σ-donating ligands to prepare novel luminescent gold(III) compounds, which can be used as the light-emitting material for OLEDs.

The luminescent gold(III) compounds of the present invention can be formed into thin films by vacuum deposition, spin-coating, inkjet printing or other known fabrication methods. Multilayer OLEDs have been fabricated using the compounds of the present invention as light-emitting material or as dopant in the emitting layer. In general, the OLEDs comprise, or consist of, an anode and a cathode, between which are the hole-transporting layer, light-emitting layer, and electron-transporting or injection layer.

The compounds described have been represented throughout by their monomeric structures. As is well known to those in the art, the compounds may also be present as dimers, trimers, dendrimers, or polymers, comprising one or more compounds of formula (I).

EXAMPLES

The present invention will be illustrated more specifically by the following non-limiting examples, it being understood that changes and variations can be made therein without deviating from the scope and the spirit of the invention as hereinafter claimed. It is also understood that various theories as to why the invention works are not intended to be limiting.

Example 1

General Synthetic Methodology

-continued wherein $R_1$ is selected from alkylalkynyl, substituted alkylalkynyl, arylalkynyl, substituted arylalkynyl, heteroarylalkynyl, substituted heteroarylalkynyl, polyalkynyl, substituted polyalkynyl, aryl, substituted aryl, substituted heteroaryl, heteroaryl, hydroxyl, alkoxyl, substituted alkoxyl, aryloxyl, substituted aryloxyl, cycloalkoxyl, substituted cycloalkoxyl, $NH_2$, unsubstituted and substituted primary amine, unsubstituted and substituted secondary amine, unsubstituted and substituted tertiary amine, carboxamide, substituted carboxamide, amide, substituted amide, imide, substituted imide, nitrile, substituted nitrile, isonitrile, substituted isonitrile, sulfanyl, sulfinyl, substituted sulfinyl, sulfonyl, and substituted sulfonyl.

Example 2

Synthesis and Characterizations

Compounds 1-13 are synthesized according to the general synthetic methodology using various ligands, and triethylamine is used as the base. The tridentate ligands of 2,6-bis (benzimidazol-2'-yl)pyridine derivatives, and the precursor compound [Au(R-bzimpy)Cl], are respectively prepared according to modified literature procedures [Froidevaux P.; Harrowfield J.-M.; Sobolev A.-N. *Inorg. Chem.* 39, 4678 (2000); Serratrice M.; Edafe F.; Mendes F.; Scopelliti R.; Zakeeruddin S.-M.; Gratzel M.; Santos I.; Cinellu M.-A.; Casini A. *Dalton Trans.*, 41, 3287 (2012)].

The synthetic procedure of compounds 1-7 and 9-11 is summarized as follows. A mixture of [Au(R-bzimpy)Cl] (0.37 mmol) and alkyne (0.74 mmol) in the presence of a catalytic amount of copper(I) iodide (10 mg, 0.05 mmol) in triethylamine (2 mL) and dichloromethane (50 mL) is stirred at room tempearture for 3 hours. After evaporation to dryness, the solid residue is purified by column chromatography on basic alumina using dichloromethane/methanol (99:1 v/v) as eluent. The collected solution is concentrated, and subjected to filtration using a plastic syringe fitted with a disposable 0.2 μm PTFE filter tip, and subsequent recrystallization by slow diffusion of diethyl ether vapor. The desired compounds are obtained as yellow solids.

The synthetic procedure of compound 8, 12 and 13 is as follows. A mixture of [Au(R-bzimpy)Cl] (0.37 mmol), 4-phenylimidazole (0.74 mmol) and triethylamine (2 mL) in dichloromethane (50 mL) is stirred at room temperature for 3 hours. After evaporation to dryness, the solid residue is purified by column chromatography on basic alumina using dichloromethane/methanol (99:1 v/v) as eluent. The collected solution is concentrated, and subjected to filtration using a plastic syringe fitted with a disposable 0.2 μm PTFE filter tip, and subsequent recrystallization by slow diffusion of diethyl ether vapor into a concentrated dichloromethane solution of the compound. The desired compound 8 is obtained as a pale orange solid.

R = H,
R' = propyl (1)
    tert-butyl (2)
    $C_6H_5$ (3)
    $C_6H_4OCH_3$-p (4)
    $C_6H_4OC_3H_7$-p (5)
    $C_6H_4CF_3$-p (6)

R = $CO_6H_{13}$,
R' = $C_6H_4OCH_3$-p (7)

(8)

X = C, Y = S, n = 1 (9)
X = C, Y = O, n = 1 (10)
X = N, Y = S, n = 2 (11)

Y = S (12)
Y = O (13)

The characteristic spectroscopic properties of compounds 1-8 are listed below:

[Au(bzimpy)(C≡C—C$_3$H$_7$)] (Compound 1)

(bzimpy=2,6-bis(benzimidazol-2'-yl)pyridine)
Yield: 18%. $^1$H NMR (400 MHz, CDCl$_3$, 298 K, relative to Me$_4$Si): δ 1.19 (t, J=7.1 Hz, 3H, —CH$_3$), 1.82 (m, 2H, —CH$_2$—), 2.74 (t, J=7.1 Hz, 2H, —CH$_2$—), 7.30 (t, J=7.9 Hz, 2H, bzimpy), 7.37 (t, J=7.9 Hz, 2H, bzimpy), 7.81 (d, J=7.9 Hz, 2H, bzimpy), 8.08 (d, J=7.9 Hz, 2H, bzimpy), 8.19 (t, J=7.9 Hz, 1H, bzimpy), 8.22 (d, J=7.9 Hz, 2H, bzimpy); positive FAB-MS: m/z 574 [M]$^+$; IR (KBr): 2182 cm$^{-1}$ (ν(C≡C)); elemental analyses calcd for C$_{24}$H$_{18}$AuN$_5$·½H$_2$O (found): C, 49.49 (49.34), H, 3.29 (3.16), N, 12.02 (11.97).

[Au(bzimpy)(C≡C-$^t$Bu)] (Compound 2)

Yield: 14%. $^1$H NMR (400 MHz, CDCl$_3$, 298 K, relative to Me$_4$Si): δ 1.54 (s, 9H, $^t$Bu), 7.31 (t, J=7.9 Hz, 2H, bzimpy), 7.38 (t, J=7.9 Hz, 2H, bzimpy), 7.82 (d, J=7.9 Hz, 2H, bzimpy), 8.11 (d, J=7.9 Hz, 2H, bzimpy), 8.24 (t, J=7.9 Hz, 1H, bzimpy), 8.33 (d, J=7.9 Hz, 2H, bzimpy); positive FAB-MS: m/z 588 [M]$^+$; IR (KBr): 2186 cm$^{-1}$ (ν(C≡C)); elemental analyses calcd for C$_{25}$H$_{20}$AuN$_5$·H$_2$O (found): C, 49.59 (49.64), H, 3.66 (3.44), N, 11.57 (11.56).

[Au(bzimpy)(C≡C—C$_6$H$_5$)] (Compound 3)

Yield: 22%. $^1$H NMR (400 MHz, CDCl$_3$, 298 K, relative to Me$_4$Si): δ 7.29 (m, 3H, —C$_6$H$_5$), 7.35 (t, J=7.9 Hz, 2H, bzimpy), 7.47 (t, J=7.9 Hz, 2H, bzimpy), 7.71 (d, J=6.5 Hz, 2H, —C$_6$H$_5$), 7.81 (d, J=7.9 Hz, 2H, bzimpy), 8.11 (d, J=7.9 Hz, 2H, bzimpy), 8.21 (t, J=7.9 Hz, 1H, bzimpy), 8.25 (d, J=7.9 Hz, 2H, bzimpy); positive FAB-MS: m/z 608 [M]$^+$; IR (KBr): 2164 cm$^{-1}$ (ν(C≡C)); elemental analyses calcd for C$_{27}$H$_{16}$AuN$_5$·½CH$_2$Cl$_2$ (found): C, 50.82 (50.49), H, 2.64 (2.81), N, 10.78 (10.87).

[Au(bzimpy)(C≡C—C$_6$H$_4$—OCH$_3$-p)] (Compound 4)

Yield: 13%. $^1$H NMR (400 MHz, CDCl$_3$, 298 K, relative to Me$_4$Si): δ 3.89 (s, 3H, OCH$_3$), 6.99 (d, J=8.6 Hz, 2H, —C$_6$H$_4$—), 7.29 (t, J=8.2 Hz, 2H, bzimpy), 7.33 (t, J=8.2 Hz, 2H, bzimpy), 7.61 (d, J=8.6 Hz, 2H, —C$_6$H$_4$—), 7.78 (d, J=8.2 Hz, 2H, bzimpy), 8.08 (d, J=8.2 Hz, 2H, bzimpy), 8.18 (t, J=8.2 Hz, 1H, bzimpy), 8.23 (d, J=8.2 Hz, 2H, bzimpy); positive FAB-MS: m/z 638 [M]$^+$; IR (KBr): 2164 cm$^{-1}$ (ν(C≡C)); elemental analyses calcd for C$_{28}$H$_{18}$AuN$_5$O·½H$_2$O (found): C, 52.02 (51.88), H, 2.96 (2.88), N, 10.83 (10.84).

[Au(bzimpy)(C≡C—C$_6$H$_4$—OC$_3$H$_7$-p)] (Compound 5)

Yield: 20%. $^1$H NMR (400 MHz, CDCl$_3$, 298 K, relative to Me$_4$Si): δ 1.10 (t, J=6.5 Hz, 3H, —CH$_3$), 1.87 (m, 2H, —CH$_2$—), 3.99 (t, J=6.5 Hz, 2H, —OCH$_2$—), 6.93 (d, J=8.6 Hz, 2H, —C$_6$H$_4$—), 7.21 (t, J=7.8 Hz, 2H, bzimpy), 7.24 (t, J=7.8 Hz, 2H, bzimpy), 7.53 (d, J=8.6 Hz, 2H, —C$_6$H$_4$—), 7.71 (d, J=7.8 Hz, 2H, bzimpy), 7.98 (d, J=7.8 Hz, 2H, bzimpy), 8.09 (t, J=7.8 Hz, 1H, bzimpy), 8.14 (d, J=7.8 Hz, 2H, bzimpy); positive FAB-MS: m/z 666 [M]$^+$; IR (KBr): 2166 cm$^{-1}$ (ν(C≡C)); elemental analyses calcd for C$_{30}$H$_{22}$AuN$_5$O (found): C, 54.14 (53.86), H, 3.33 (3.36), N, 10.52 (10.52).

[Au(bzimpy)(C≡C—C$_6$H$_4$—CF$_3$-p)] (Compound 6)

Yield: 19%. $^1$H NMR (400 MHz, CDCl$_3$, 298 K, relative to Me$_4$Si): δ 7.31 (t, J=7.9 Hz, 2H, bzimpy), 7.35 (t, J=7.9 Hz, 2H, bzimpy), 7.72 (d, J=8.8 Hz, 2H, —C$_6$H$_4$—), 7.77 (d, J=8.8 Hz, 2H, —C$_6$H$_4$—), 7.81 (d, J=7.9 Hz, 2H, bzimpy), 8.10 (d, J=7.9 Hz, 2H, bzimpy), 8.15 (d, J=7.9 Hz, 2H, bzimpy), 8.24 (t, J=7.9 Hz, 1H, bzimpy); positive FAB-MS: m/z 676 [M]$^+$; IR (KBr): 2172 cm$^{-1}$ (ν(C≡C)); elemental analyses calcd for C$_{28}$H$_{15}$AuF$_3$N$_5$ (found): C, 49.79 (49.40), H, 2.24 (2.34), N, 10.37 (10.29).

[Au(C$_6$H$_{13}$O-bzimpy)(C≡C—C$_6$H$_4$—OCH$_3$-p)] (Compound 7)

Yield: 20%. $^1$H NMR (400 MHz, CDCl$_3$, 298 K, relative to Me$_4$Si): δ 0.95 (t, J=6.5 Hz, 3H, —CH$_3$), 1.38 (m, 4H, —CH$_2$—), 1.49 (m, 2H, —CH$_2$—), 1.91 (m, 2H, —CH$_2$—), 3.89 (s, 3H, —OCH$_3$), 4.25 (t, J=6.5 Hz, 2H, —OCH$_2$—), 6.97 (d, J=8.8 Hz, 2H, —C$_6$H$_4$—), 7.23 (t, J=8.1 Hz, 2H, bzimpy), 7.31 (t, J=8.1 Hz, 2H, bzimpy), 7.49 (s, 2H, bzimpy), 7.60 (d, J=8.8 Hz, 2H, —C$_6$H$_4$—), 7.75 (d, J=8.1 Hz, 2H, bzimpy), 8.21 (d, J=8.1 Hz, 2H, bzimpy); positive FAB-MS: m/z 738 [M]$^+$; elemental analyses calcd for C$_{34}$H$_{30}$AuN$_5$O$_2$ (found): C, 55.36 (55.08), H, 4.10 (4.27), N, 9.49 (9.29).

[Au(bzimpy)(4-phenylimidazole)] (Compound 8)

Yield: 19%. $^1$H NMR (400 MHz, CDCl$_3$, 298 K, relative to Me$_4$Si): δ 6.29 (d, J=7.9 Hz, 2H, bzimpy), 7.06 (t, J=7.9 Hz, 2H, bzimpy), 7.17 (t, J=7.9 Hz, 2H, bzimpy), 7.35 (t, J=7.5 Hz, 1H, —C$_6$H$_5$), 7.49 (t, J=7.5 Hz, 2H, —C$_6$H$_5$), 7.72 (d, J=7.9 Hz, 2H, bzimpy), 7.85 (s, 1H, imidazole), 8.01 (d, J=7.5 Hz, 2H, —$C_6H_5$), 8.06 (s, 1H, imidazole), 8.09 (d, J=7.9 Hz, 2H, bzimpy), 8.25 (t, J=7.9 Hz, 1H, bzimpy); positive FAB-MS: m/z 650 [M]$^+$.

Example 3

UV-Vis Absorption Properties

Gold(III) compounds of the present invention exhibit rich luminescence at both room temperature and low temperature in various media. The UV-vis absorption data of compounds 1-8 are summarized in Table 1.

Compounds 1-7 show intense absorption bands at 320-330 nm. Compounds 1-6, which have the same tridentate ligand but different alkynyl ligands, also show vibronic-structured absorptions with similar shape and energy at 380-450 nm, indicating that the lower-energy absorption band is rather insensitive to the nature of the alkynyl ligands. This, together with the observation of a similar absorption band for the chloro counterpart, [Au(bzimpy)Cl], allow the assignment of the lower-energy band as the metal-perturbed intraligand π-π* transition of the 2,6-bis(benzimidazol-2'-yl)pyridine ligand in the compounds, indicating the involvement of some charge transfer character from the benzimidazole moiety to the pyridyl unit. The observation of a less structured absorption spectrum and a hypsochromic shift in the lower-energy absorption for compound 7, which has a —$OC_6H_{13}$ group on the pyridine ring in the tridentate ligand but the same alkynyl ligand as in compound 4, also indicates the assignment of the lower-energy absorption.

Figure 1:
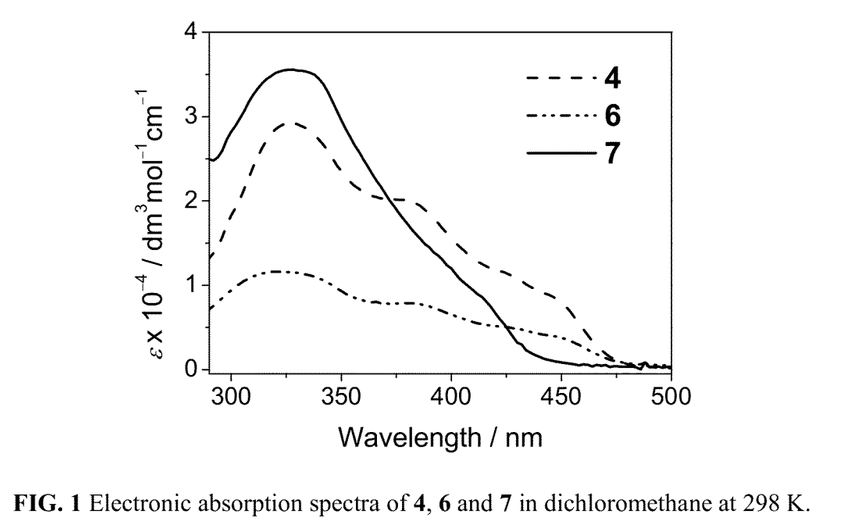
FIG. 1 shows the electronic absorption spectra of Compounds 4, 6 and 7 in dichloromethane at 298 K.

FIG. 1 shows the electronic absorption spectra of Compounds 4, 6 and 7 in dichloromethane at 298 K.

TABLE 1

UV-Vis absorption data for compounds 1-7

| compound | Absorption$^a$ $\lambda_{max}$/nm ($\epsilon_{max}$/dm$^3$mol$^{-1}$cm$^{-1}$) |
|---|---|
| 1 | 328 (12525), 378(8405), 424(5100), 446(3780) |
| 2 | 328(26535), 378(18035), 424(11000), 446(8275) |
| 3 | 322(26420), 380(17040), 426(10090), 448(7550) |
| 4 | 328(29220), 380(20080), 426(11330), 448(8380) |
| 5 | 328(21950), 380(15310), 426(8860), 448(6645) |
| 6 | 322(11620), 382(7890), 426(5025), 448(3910) |
| 7 | 328(35580), 412(8925) |

$^a$In dichloromethane at 298K.

Example 4

An OLED device according to an embodiment of the invention is constructed in the following manner:
a) a transparent anode ITO-coated glass substrate is cleaned ultrasonically in a commercial detergent, rinsed in deionized water, and then dried in an oven. The substrate is subsequently subjected to an UV-ozone treatment for 25 minutes;
b) a 40-nm thick poly(3,4-ethylenedioxythiophene):poly(4-styrene-surlfonate) (PEDOT:PSS) hole-transporting layer is spin-coated on the ITO-coated glass substrate;
c) a 30-nm thick light-emitting layer is spin-coated on the PEDOT:PSS layer, in which 5 wt % compound 2 is doped into a light-emitting MCP layer;
d) the substrate is put into a vacuum chamber, and the chamber is pumped down to 5×10$^{-6}$ mbar;
e) a 30-nm thick bis(2-methyl-8-quinolinolate)-4-(phenylphenolate)aluminum (BAlq) is deposited on the doped MCP light-emitting layer;
f) a 0.8-nm thick LiF and a 100-nm thick aluminum are deposited on the BAlq layer as electron-injecting cathode.

BAlq, LiF and Al are prepared by thermal evaporation from tantalum boats. Deposition rates are monitored with a quartz oscillation crystal and controlled at 0.1-0.2 nm/s for both organic and metal layers. Current density-voltage-luminance characteristics of organic EL devices are measured with a programmable Keithley model 2420 power source and a Spectrascan PR-655 colorimeter under ambient air conditions.

Figure 2:
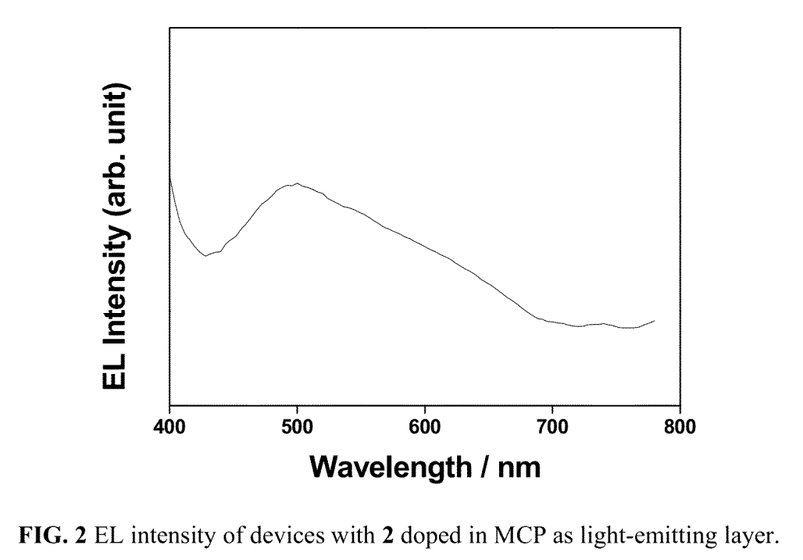
FIG. 2 shows the EL intensity of devices with Compound 2 doped in m-(N,N'-dicarbazole)benzene (MCP) as a light-emitting layer.

FIG. 2 shows the EL spectrum for device of Example 4, in which a broad EL spectum with emission peak at ca. 498 nm is obtained. This demonstrates that the luminescent gold(III) compounds according to embodiments of the present invention can be effectively used as phosphorescent dopants for the fabrication of OLEDs.

We claim:
1. A compound, which is any of Compounds 11-13:

X = N, Y = S, n = 2 (11)

Y = S (12)
Y = O (13)

2. A dimer, trimer, oligomer or polymer formed from at least two compounds, wherein each of said compounds is a compound of claim 1, wherein said compounds are connected through one or more bridging substituents.

3. A layer comprising a compound of claim 1.

4. A layer according to claim 3, wherein at least one compound is deposited by sublimation, vacuum deposition, spin-coating, or inkjet printing to form said layer.

5. A compound according to claim 1, wherein the compound has photoluminescence properties.

6. A compound according to claim 1, wherein the compound has electroluminescence properties.

7. A compound according to claim 1, wherein the compound can be fabricated into an organic light-emitting device.

8. A compound of claim 1, wherein the compound serves as the light-emitting layer of an organic light-emitting device.

9. A compound of claim 1, wherein the compound serves as a dopant in the light-emitting layer of an organic light-emitting device.

10. A compound of claim 9, wherein luminescence energy of the compound varies with the concentration of the dopant.

11. An organic light-emitting device comprising a layer of the compound of claim 1.

12. An organic light-emitting device comprising a structure of anode/hole-transporting layer/light-emitting layer/electron-transporting layer/cathode, wherein the light-emitting layer comprises the compound of claim 1.

* * * * *

UNITED STATES PATENT AND TRADEMARK OFFICE
CERTIFICATE OF CORRECTION

PATENT NO. : 8,987,450 B2
APPLICATION NO. : 13/838185
DATED : March 24, 2015
INVENTOR(S) : Yam et al.

Page 1 of 1

It is certified that error appears in the above-identified patent and that said Letters Patent is hereby corrected as shown below:

In the Specification

Column 9,
Line 13, "application Ser. No." should read --Application No.--

Column 11,
Line 22, "R=$CO_6H_{13}$," should read --R=$OC_6H_{13}$,--

Column 13,
Line 57, "C, 50.82" should read --C 50.82--
Line 57, "H, 2.64" should read --H 2.64--
Line 58, "N, 10.78" should read --N 10.78--

Column 14,
Lines 24-25, "C, 52.02... H, 2.96... N, 10.83" should read --C 52.02... H 2.96... N 10.83--
Lines 36-37, "C, 54.14... H, 3.33... N, 10.52" should read --C 54.14... H 3.33... N 10.52--
Lines 47-48, "C, 49.79... H, 2.24... N, 10.37" should read --C 49.79... H 2.24... N 10.37--
Lines 60-61, "C, 55.36... H, 4.10... N, 9.49" should read --C 55.36... H 4.10... N 9.49--

Signed and Sealed this
First Day of December, 2015

Michelle K. Lee
*Director of the United States Patent and Trademark Office*